US00PP31306P3

(12) United States Plant Patent
Wain

(10) Patent No.: US PP31,306 P3
(45) Date of Patent: Dec. 31, 2019

(54) ***CHRYSANTHEMUM* PLANT NAMED 'DOMMERTRUP'**

(50) Latin Name: ***Chrysanthemum* X *morifolium***
Varietal Denomination: Dommertrup

(71) Applicant: DUMMEN GROUP B.V., De Lier (NL)

(72) Inventor: Peter Wain, Locks Heath (GB)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/350,594

(22) Filed: Dec. 7, 2018

(65) Prior Publication Data

US 2019/0183021 P1 Jun. 13, 2019

Related U.S. Application Data

(60) Provisional application No. 62/708,405, filed on Dec. 8, 2017.

(51) Int. Cl.
*A01H 5/02* (2018.01)
*A01H 6/14* (2018.01)

(52) U.S. Cl.
USPC ..... Plt./291
CPC ..... *A01H 6/1424* (2018.05)

(58) Field of Classification Search
USPC ..... Plt./263.1, 284, 286, 287, 291
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Chrysanthemum* plant named 'Dommertrup', characterized by its upright to outwardly spreading and uniformly and broadly mounded plant habit; moderately vigorous growth habit; freely branching habit; dense and full plant form; uniform and freely flowering habit; decorative-type inflorescences with light purple-colored ray florets; mid-season flowering habit, grown under natural season conditions, plants begin flowering in early September in the United Kingdom; and good garden performance.

1 Drawing Sheet

Botanical designation: *Chrysanthemum* X *morifolium*.
Cultivar denomination: 'DOMMERTRUP'.

BACKGROUND OF THE INVENTION

The present invention relates to a new and distinct *Chrysanthemum* plant, botanically known as *Chrysanthemum* X *morifolium*, commercially grown as a garden *Chrysanthemum* plant, referred to as code number 66569 in U.S. Provisional Patent Application Ser. No. 62/708,405 and hereinafter referred to by the name 'Dommertrup'.

The new *Chrysanthemum* plant is a product of a planned breeding program conducted by the Inventor in Fareham, Hampshire, United Kingdom. The objective of the breeding program is to create new garden *Chrysanthemum* plants with numerous attractive inflorescences.

The new *Chrysanthemum* plant originated from a cross-pollination made in January, 2013 by the Inventor in Fareham, Hampshire, United Kingdom of a proprietary selection of *Chrysanthemum* X *morifolium* identified as code number 802483, not patented, as the female, or seed, parent with a proprietary selection of *Chrysanthemum* X *morifolium* identified as code number 802067, not patented, as the male, or pollen, parent. The new *Chrysanthemum* plant was discovered and selected by the Inventor as a single flowering plant from within the progeny of the stated cross-pollination in a controlled greenhouse environment in Fareham, Hampshire, United Kingdom in September, 2013.

Asexual reproduction of the new *Chrysanthemum* plant by terminal vegetative cuttings was first conducted in Fareham, Hampshire, United Kingdom in December, 2013. Asexual reproduction by terminal vegetative cuttings has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Dommertrup'. These characteristics in combination distinguish 'Dommertrup' as a new and distinct *Chrysanthemum* plant:

1. Upright to outwardly spreading and uniformly and broadly mounded plant habit.
2. Moderately vigorous growth habit.
3. Freely branching habit; dense and full plant form.
4. Uniform and freely flowering habit.
5. Decorative-type inflorescences with light purple-colored ray florets.
6. Mid-season flowering habit, grown under natural season conditions, plants begin flowering in early September in the United Kingdom.
7. Good garden performance.

Plants of the new *Chrysanthemum* can be compared to plants of the female parent selection. Plants of the new *Chrysanthemum* differ primarily from plants of the female parent selection in the following characteristics:

1. Plants of the new *Chrysanthemum* are larger than plants of the female parent selection.
2. Plants of the new *Chrysanthemum* have larger inflorescences than plants of the female parent selection.

Plants of the new *Chrysanthemum* can be compared to plants of the male parent selection. Plants of the new *Chrysanthemum* differ primarily from plants of the male parent selection in the following characteristics:

1. Plants of the new *Chrysanthemum* have decorative type inflorescences whereas plants of the male parent selection have semi-decorative type inflorescences.
2. Plants of the new *Chrysanthemum* and the male parent selection differ in ray floret color as plants of the new *Chrysanthemum* have inflorescences with light purple-colored ray florets whereas plants of the male parent selection have inflorescences with coral pink-colored ray florets.

Plants of the new *Chrysanthemum* can be compared to plants of *Chrysanthemum* X *morifolium* 'Fichrysunaub', disclosed in U.S. Plant patent application Ser. No. 15/732,517. In side-by-side comparisons, plants of the new *Chrysanthemum* differ primarily from plants of 'Fichrysunaub' in the following characteristics:

1. Plants of the new *Chrysanthemum* flower later than plants of 'Fichrysunaub'.
2. Plants of the new *Chrysanthemum* and 'Fichrysunaub' differ in ray floret color as plants of the new *Chrysanthemum* have inflorescences with light purple-colored ray florets whereas plants of 'Fichrysunaub' have inflorescences with deep red purple-colored ray florets.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. Colors in the photograph may differ slightly from the color values cited in the detailed botanical description which accurately describe the colors of the new *Chrysanthemum* plant.

The photograph is a top perspective view of a typical flowering plant of 'Dommertrup' grown in a container.

DETAILED BOTANICAL DESCRIPTION

The aforementioned photograph and following observations and measurements describe plants grown during the winter in 19-cm containers in a glass-covered greenhouse in Fareham, Hampshire, United Kingdom and under cultural practices typical of commercial garden *Chrysanthemum* production. During the production of the plants, day and night temperatures ranged from 17° C. to 21° C. and light levels averaged 6,000 lux. Plants were grown under long day/short night conditions for about seven weeks (including propagation period) and then grown under short day/long night conditions to induce inflorescence initiation and development. Plants were 14 weeks old when the photograph and detailed description were taken. In the following description, color references are made to The Royal Horticultural Society Colour Chart, Fifth Edition, except where general terms of ordinary dictionary significance are used.

Botanical classification: *Chrysanthemum* X *morifolium* 'Dommertrup'.

Parentage:

*Female, or seed, parent*.—Proprietary selection of *Chrysanthemum* X *morifolium* identified as code number 802483, not patented.

*Male, or pollen, parent*.—Proprietary selection of *Chrysanthemum* X *morifolium* identified as code number 802067, not patented.

Propagation:

*Type*.—Terminal vegetative cuttings.

*Time to initiate roots, summer*.—About ten days at temperatures about 21° C.

*Time to initiate roots, winter*.—About twelve days at temperatures about 21° C.

*Time to produce a rooted young plant, summer*.—About three weeks at temperatures about 21° C.

*Time to produce a rooted young plant, winter*.—About four weeks at temperatures about 21° C.

*Root description*.—Medium in thickness, fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Herbaceous decorative-type garden *Chrysanthemum*; stems upright to outwardly spreading giving a uniformly broadly mounded appearance to the plant; numerous lateral branches and relatively short internodes, dense and full plant form; moderately vigorous growth habit and medium growth rate.

*Plant height*.—About 15 cm.

*Plant width*.—About 32 cm.

*Branching habit*.—Freely branching habit; about 13 lateral branches develop after removal of terminal apex (pinching).

*Lateral branches*.—Length: About 11 cm. Diameter: About 2 mm. Internode length: About 9 mm. Strength: Strong. Aspect: About 5° from vertical and then bending upwardly. Texture: Fine pubescence. Color: Close to 146D.

Leaf description:

*Arrangement*.—Alternate, simple.

*Length*.—About 4.2 cm.

*Width*.—About 2.2 cm.

*Shape*.—Palmately-lobed; roughly ovate with three to five lobes.

*Apex*.—Broadly acute.

*Base*.—Attenuate.

*Margin*.—Slightly dentate and palmately lobed; sinuses between lateral lobes mostly divergent.

*Texture, upper and lower surfaces*.—Fine pubescence; slightly rough.

*Venation pattern*.—Pinnate.

*Color*.—Developing leaves, upper surface: Close to 137B. Developing leaves, lower surface: Close to 137C. Fully expanded leaves, upper surface: Close to N137C; venation, close to 146B. Fully expanded leaves, lower surface: Close to 147B; venation, close to 146B.

*Petioles*.—Length: About 7 mm. Diameter: About 3 mm. Texture, upper and lower surfaces: Fine pubescence; slightly rough. Color, upper and lower surfaces: Close to 146B.

Inflorescence description:

*Form and flowering habit*.—Decorative-type inflorescence form with ligulate-shaped ray florets; inflorescences borne on terminals above and beyond the foliar plane; disc and ray florets arranged acropetally on a capitulum; freely flowering habit with about 96 inflorescences developing per plant during the flowering season.

*Fragrance*.—Mildly fragrant; pungent, herbaceous.

*Flowering response*.—Mid-season flowering habit, plants exposed to natural season conditions begin flowering in early September in the United Kingdom; plants flower uniformly and continuously during the flowering season.

*Inflorescence longevity*.—Inflorescences maintain good color and substance for about three to five weeks on the plant; inflorescences persistent.

*Inflorescence buds*.—Height: About 4 mm. Diameter: About 6 mm. Shape: Oblate. Color: Close to 137B.

*Inflorescence diameter*.—About 5.5 cm.

*Inflorescence height*.—About 1.8 cm.

*Disc diameter*.—Disc floret development has not been observed on plants of the new *Chrysanthemum*.

*Receptacles*.—Height: About 3 mm. Diameter: About 3 mm. Shape: Oblate. Color: Close to 145B.

*Ray florets*.—Number of ray florets per inflorescence: About 175 arranged in about nine whorls. Orientation: Initially upright, then about 80° from vertical; weakly concave. Length: About 2 cm. Width: About 5 mm. Shape: Ligulate. Apex: Emarginate. Base: Fused into a short tube. Margin: Entire. Texture, upper and lower surfaces: Smooth, glabrous; double-keeled. Color: When opening, upper surface: Close to 77D. When opening, lower surface: Close to 84C. Fully opened, upper surface: Close to 75B; color becoming closer to 76B with development. Fully opened, lower surface: Close to 76C; color does not change with development.

*Phyllaries*.—Number of phyllaries per inflorescence: About 20 arranged in about four whorls. Length: About 7 mm. Width: About 2 mm. Shape: Lanceolate. Apex: Acute. Base: Obtuse. Margin: Entire. Texture, upper surface: Smooth, glabrous; waxy. Texture, lower surface: Fine pubescence; waxy. Color, upper surface: Close to 143A. Color, lower surface: Close to 137B.

*Peduncles*.—Length, terminal peduncle: About 2.5 cm. Diameter, terminal peduncle: About 2 mm. Angle: Erect to about 5° from vertical. Strength: Moderately strong; flexible. Texture: Densely pubescent. Color: Close to 143A.

*Reproductive organs*.—Androecium: None observed. Gynoecium: Present only on ray florets. Pistil length: About 5 mm. Stigma shape: Bi-parted. Stigma color: Close to 1B. Style length: About 4 mm. Style color: Close to 1D. Ovary color: Close to NN155A.

*Seeds and fruits*.—To date, seed and fruit production has not been observed on plants of the new *Chrysanthemum*.

Pathogen & pest resistance: To date, resistance to pathogens and pests common to *Chrysanthemum* plants has not been observed on plants of the new *Chrysanthemum*.

Garden performance: Plants of the new *Chrysanthemum* have demonstrated good garden performance and to tolerate temperatures from about 0° C. to about 35° C.

It is claimed:

1. A new and distinct *Chrysanthemum* plant named 'Dommertrup' as illustrated and described.

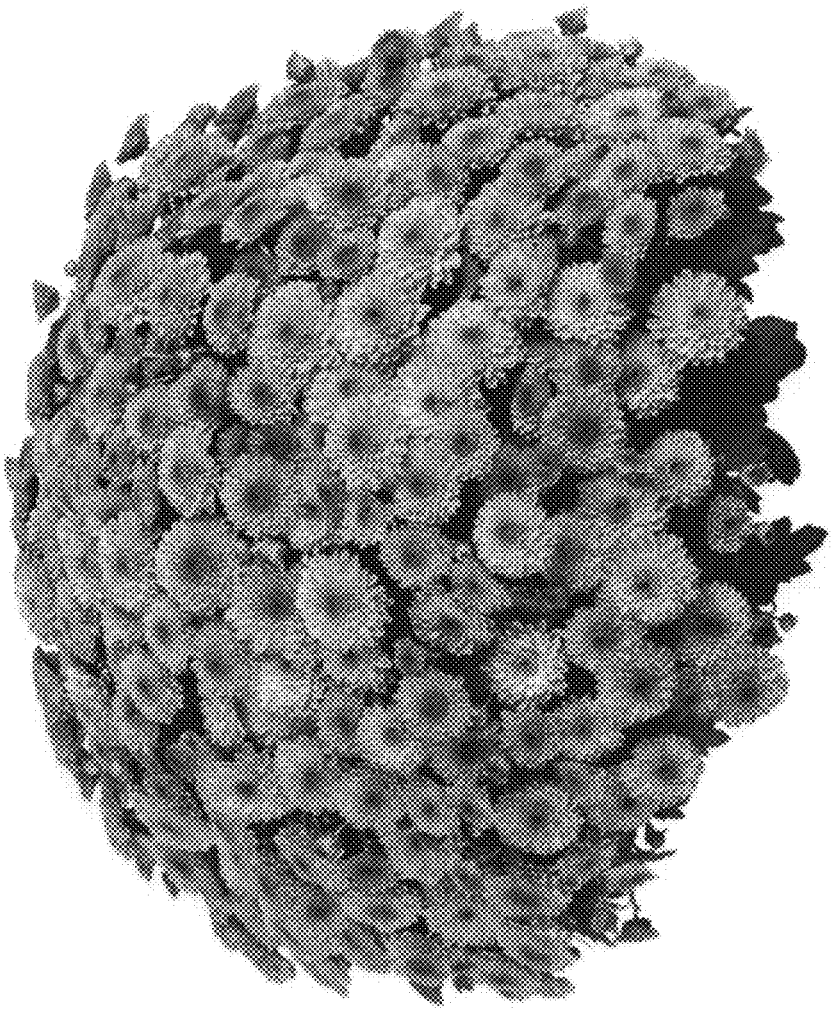

* * * * *